(12) United States Patent
Hwang et al.

(10) Patent No.: US 7,160,921 B2
(45) Date of Patent: Jan. 9, 2007

(54) REDUCTION OF HAIR GROWTH

(75) Inventors: Cheng Shine Hwang, Framingham, MA (US); James P. Henry, Mendon, MA (US); Gurpreet S. Ahluwalia, Newton, MA (US); Douglas Shander, Acton, MA (US)

(73) Assignee: The Gillette Company, Boston, MA (US)

(*) Notice: Subject to any disclaimer, the term of this patent is extended or adjusted under 35 U.S.C. 154(b) by 419 days.

(21) Appl. No.: 10/636,466

(22) Filed: Aug. 7, 2003

(65) Prior Publication Data

US 2004/0131568 A1    Jul. 8, 2004

Related U.S. Application Data

(63) Continuation-in-part of application No. 10/430,988, filed on May 6, 2003, now abandoned, which is a continuation-in-part of application No. 10/059,466, filed on Jan. 29, 2002, now abandoned.

(51) Int. Cl.
  *A61K 31/20* (2006.01)
  *A61K 31/19* (2006.01)
  *A61K 8/02* (2006.01)
  *A61K 8/18* (2006.01)

(52) U.S. Cl. ............ 514/559; 424/70.1; 424/424; 514/572

(58) Field of Classification Search ............ None
See application file for complete search history.

(56) References Cited

U.S. PATENT DOCUMENTS

| | | | |
|---|---|---|---|
| 3,426,137 A | 2/1969 | Philpitt et al. | |
| 4,039,669 A | 8/1977 | Beyler et al. | |
| 4,139,638 A | 2/1979 | Neri et al. | |
| 4,161,540 A | 7/1979 | Neri et al. | |
| 4,191,775 A | 3/1980 | Glen | |
| 4,269,831 A | 5/1981 | Ferrari et al. | |
| 4,370,315 A | 1/1983 | Greff et al. | |
| 4,439,432 A | 3/1984 | Peat | |
| 4,499,294 A * | 2/1985 | Maryanoff | 549/519 |
| 4,508,714 A | 4/1985 | Cecic et al. | |
| 4,517,175 A | 5/1985 | Iwabuchi et al. | |
| 4,720,489 A | 1/1988 | Shander | |
| 4,885,289 A | 12/1989 | Breuer et al. | |
| 4,935,231 A | 6/1990 | Pigiet | |
| 4,935,450 A * | 6/1990 | Cone, Jr. | 514/728 |
| 5,095,007 A | 3/1992 | Ahluwalia | |
| 5,096,911 A | 3/1992 | Ahluwalia et al. | |
| 5,132,293 A | 7/1992 | Shander et al. | |
| 5,143,925 A | 9/1992 | Shander et al. | |
| 5,189,212 A | 2/1993 | Ruenitz | |
| 5,271,942 A | 12/1993 | Heverhagen | |
| 5,300,284 A | 4/1994 | Wiechers et al. | |
| 5,328,686 A | 7/1994 | Shander et al. | |
| 5,362,748 A | 11/1994 | Schwen et al. | |
| 5,364,885 A | 11/1994 | Ahluwalia et al. | |
| 5,411,991 A | 5/1995 | Shander et al. | |
| 5,422,371 A * | 6/1995 | Liao et al. | 514/560 |
| 5,444,090 A | 8/1995 | Ahluwalia | |
| 5,455,234 A | 10/1995 | Ahluwalia et al. | |
| 5,468,476 A | 11/1995 | Ahluwalia et al. | |
| 5,474,763 A | 12/1995 | Shander et al. | |
| 5,554,608 A | 9/1996 | Ahluwalia et al. | |
| 5,645,825 A | 7/1997 | Hillebrand et al. | |
| 5,648,394 A | 7/1997 | Boxall et al. | |
| 5,652,273 A | 7/1997 | Henry et al. | |
| 5,674,477 A | 10/1997 | Ahluwalia | |
| 5,728,736 A | 3/1998 | Shander et al. | |
| 5,776,442 A | 7/1998 | Ahluwalia | |
| 5,824,665 A | 10/1998 | Henry et al. | |
| 5,840,752 A | 11/1998 | Henry et al. | |
| 5,908,867 A | 6/1999 | Henry et al. | |
| 5,939,458 A | 8/1999 | Henry et al. | |
| 5,958,946 A | 9/1999 | Styczynski et al. | |
| 5,962,466 A | 10/1999 | Styczynski et al. | |
| 6,020,006 A | 2/2000 | Styczynski et al. | |
| 6,037,326 A | 3/2000 | Styczynski et al. | |
| 6,060,471 A | 5/2000 | Styczynski et al. | |
| 6,093,748 A | 7/2000 | Ahluwalia et al. | |
| 6,121,269 A | 9/2000 | Henry et al. | |
| 6,218,435 B1 | 4/2001 | Henry et al. | |
| 6,235,737 B1 | 5/2001 | Styczynski et al. | |
| 6,239,170 B1 | 5/2001 | Ahluwalia et al. | |
| 6,248,751 B1 | 6/2001 | Ahluwalia et al. | |
| 6,284,234 B1 * | 9/2001 | Niemiec et al. | 424/78.07 |
| 6,299,865 B1 | 10/2001 | Styczynski et al. | |

FOREIGN PATENT DOCUMENTS

| | | |
|---|---|---|
| EP | 0 413 528 B1 | 8/1990 |
| EP | 0 532 219 A2 | 9/1992 |
| EP | 0 872 248 A2 | 10/1998 |
| EP | 0 943 311 A2 | 9/1999 |

(Continued)

OTHER PUBLICATIONS

Kuhajda, F.P., et al., "Synthesis and antitumor activity of an inhibitor of fatty acid synthase", Proc Natl Acad Sci U S A, 2000. 97(7): p. 3450-4.

(Continued)

*Primary Examiner*—Sreeni Padmanabhan
*Assistant Examiner*—Marina Lamm
(74) *Attorney, Agent, or Firm*—Andrew J. Hagerty; Tara M. Rosnell; Brian M. Bolam

(57) ABSTRACT

Mammalian hair growth can be reduced by topical application of an inhibitor of fatty acid metabolism.

13 Claims, 1 Drawing Sheet

FOREIGN PATENT DOCUMENTS

| | | |
|---|---|---|
| EP | 0 943 311 A3 | 5/2000 |
| GB | 1 458 349 | 12/1976 |
| JP | 2001026522 | 1/2001 |
| WO | WO 95/33439 | 12/1995 |
| WO | WO 98/02134 | 1/1998 |

OTHER PUBLICATIONS

Lin, S. et al., "Inhibition of 4-hydroxyphenylpyruvate dioxygenase by sethoxydim, a potent inhibitor of acetyl-coenzyme A carboxylase", Bioorg Med Chem Lett, 1999. 9(4): p. 551-4.

Kennedy, J.A. et al., "Effect of trimetazidine on carnitine palmitoyltransferase-1 in the rat heart", Cardiovasc Drugs Ther, 1998. 12(4): p. 359-63.

Broadway, N.M., "Novel methylenecyclopropyl-based acyl-CoA dehydrogenase inhibitor", FEBS Lett, 1998. 437(1-2): p. 122-6.

Botchkarev et al., "A New Role for Neurotrophin-3", American Journal of Pathology, vol. 153, pp. 785-799, 1998.

Botchkarev et al., "Neurotrophin-3 Involvement in the Regulation of Hair Follicle Morphogenesis", The Journal of Investigative Dermatology, vol. 111, No. 2, pp. 279-285, 1998.

Hoffmann et al., "Interleukin-1 β-Induced Inhibition of Hair Growth In Vitro Is Mediated by Cyclic AMP", The Journal of Investigative Dermatology, vol. 108, pp. 40-42, 1997.

Kennedy et al., "Inhibition of carnitine palmitoyltransferase-1 in rat heart and liver by perhexiline and amiodarone", Biochem Pharmacol, 1996. 52(2): p. 273-80.

Cummings, J.G. et al., "3-Methyleneoctanoyl-CoA and 3-methyl-trans-2-octenoyl-CoA: two new mechanism-based inhibitors of medium chain acyl-CoA dehydrogenase from pig kidney" Biochemistry, 1994. 33(3): p. 788-97.

Saeed, A., et al., "Carnitine acyltransferase enzymic catalysis requires a positive charge on the carnitine cofactor", Arch Biochem Biophys, 1993. 305(2): p. 307-12.

Tserng, K.Y. et al., "Spiropentaneacetic acid as a specific inhibitor of medium-chain acyl-CoA dehydrogenase", Biochemistry, 1991. 30(44): p. 10755-60.

Messenger, Andrew G., "The Control of Hair Growth: An Overview", The Journal of Investigative Dermatology, vol. 101, No. 1, pp. 4s-9s, 1993.

Weinberg et al., "Reconstitution of Hair Follicle Development In Vitro: Determination of Follicle Formation, Hair Growth, and Hair Quality by Dermal Cells", The Journal of Investigative Dermatology, vol. 100, pp. 229-236, 1993.

Lilly, K., et al., "Effect of etomoxiryl-CoA on different carnitine acyltransferases", Biochem Pharmacol, 1992. 43(2): p. 353-61.

Rose-Kahn, G. et al., "Inhibition of rat liver acetyl-CoA carboxylase by beta, beta'-tetramethyl-substituted hexadecanedioic acid", (MEDICA 16). Biochim Biophys Acta, 1990. 1042(2): p. 259-64.

Kashfi, K., et al., "Inhibition of mitochondrial carnitine palmitoyltransferases by adriamycin and adriamycin analogues", Biochem Pharmacol, 1990. 40(7): p. 1441-8.

Gandour, R.D., et al., "Hemipalmitoylcarnitinium, a strong competitive inhibitor of purified hepatic carnitine palmitoyltransferase", Arch Biochem Biophys, 1988. 267(2): p. 515-20.

Olubadewo, J.O. et al., "Effects of 8-N,N-diethylamino-octyl-3,4,5-trimethoxybenzoate (TMB-8) HCl and verapamil on the metabolism of free fatty acid by hepatocytes", Biochem Pharmacol, 1988. 37(8): p. 1463-71.

Li, J.X. et al., "4-Bromo-2-octenoic acid specifically inactivates 3-ketoacyl-CoA thiolase and thereby fatty acid oxidation in rat liver mitochondria", Biochemistry, 1988. 27(16): p. 5995-6000.

Shinagawa, S., et al., "Chemistry and inhibitory activity of long chain fatty acid oxidation of emeriamine and its analogues", J Med Chem, 1987. 30(8): p. 1458-63.

Cook, G.A., "The hypoglycemic sulfonylureas glyburide and tolbutamide inhibit fatty acid oxidation by inhibiting carnitine palmitoyltransferase", J Biol Chem, 1987. 262(11): p. 4968-72.

el-Aleem, S.A. et al., "Evaluation of inhibitors of fatty acid oxidation in rat myocytes", Biochem Pharmacol, 1987. 36(24): p. 4307-12.

Whittington, F.M., et al., "Effect of sodium 2-n-pentadecyl-benzimidazole-5-carboxylate (M & B 35347B), an inhibitor of acetyl-CoA carboxylase, on lipogenesis and fat deposition in obese hyperglycaemic (ob/ob) and lean mice", Int J Obes, 1987. 11(6): p. 619-29.

Ebling, F. John G., "The Biology of Hair", Dermatologic Clinics, vol. 5, No. 3, pp. 467-481, 1987.

Jenkins et al., "Antiketogenic and hypoglycemic effects of aminocarnitine and acylaminocarnitines", Proc Natl Acad Sci U S A, 1986. 83(2): p. 290-4.

Gandour, R.D., et al., "Active-site probes of carnitine acyltransferases. Inhibition of carnitine acetyltransferase by hemiacetylcarnitinium, a reaction intermediate analogue", Biochem Biophys Res Commun, 1986. 138(2): p. 735-41.

Stephens, T.W., et al., "Two mechanisms produce tissue-specific inhibition of fatty acid oxidation by oxfenicine" Biochem J, 1985. 227(2): p. 651-60.

Bauche, F. et al., "Inhibition in vitro of acyl-CoA dehydrogenases by 2-mercaptoacetate in rat liver mitochondria", Biochem J, 1983. 215(3): p. 457-64.

Schulz, H., "Metabolism of 4-pentenoic acid and inhibition of thiolase by metabolites of 4-pentenoic acid", Biochemistry, 1983. 22(8): p. 1827-32.

Hattori et al., "Biochemical Analysis of Hair Growth From the Aspects of Aging and Enzyme Activities", The Journal of Dermatology, vol. 10, pp. 45-54, 1983.

Olowe, Y. et al., "4-Bromocrotonic acid, an effective inhibitor of fatty acid oxidation and ketone body degradation in rat heart mitochondria. On the rate-determining step of beta-oxidation and ketone body degradation in heart", J Biol Chem, 1982. 257(10): p. 5408-13.

Tutwiler, G.F. et al., "2-Tetradecylglycidic acid. Methods Enzymol", 1981. 72: p. 533-51.

Barlett, K. et al., "Inhibition of mitochondrial beta-oxidation at the stage of carnitine palmitoyltransferase I by the coenzyme A ester of some substituted hypoglycaemic oxiran-2-carboxylic acids", Biochemical Soc. Transactions, 1981. 9: p. 574-575.

Wenz, A., C. Thorpe, and S. Ghisla, "Inactivation of general acyl-CoA dehydrogenase from pig kidney by a metabolite of hypoglycin", A. J Biol Chem, 1981. 256(19): p. 9809-12.

McCune, S.A. et al., "Mechanism responsible for 5-(tetradecyloxy)-2-furoic acid inhibition of hepatic lipogenesis", J Biol Chem, 1979. 254(20): p. 10095-101.

Jeffcoat, R. et al., "Studies on the inhibition of the desaturases by cyclopropenoid fatty acids", Lipids, 1977. 12(6): p. 480-5.

Lien, E.L. et al., "Effects of an acetyl-coenzyme A carboxylase inhibitor and a sodium-sparing diuretic on aldosterone-stimulated sodium transport, lipid synthesis, and phospholipid fatty acid composition in the toad urinary bladder", Biochemistry, 1975. 14(12): p. 2749-54.

Chase et al., "Specific inhibition of mitochondrial fatty acid oxidation by 2-bromopalmitate and its coenzyme A and carnitine esters", Biochem J, 1972. 129(1): p. 55-65.

Christophersen et al., "Erucic acid—an inhibitor of fatty acid oxidation in the heart", Biochim Biophys Acta, 1972. 280(4): p. 506-14.

Vance, D., et al., "Inhibition of fatty acid synthetases by the antibiotic cerulenin", Biochem Biophys Res Commun, 1972. 48(3): p. 649-56.

Adachi et al., "Human Hair Follicles: Metabolism and Control Mechanisms", Journal of the Society of Cosmetic Chemists, vol. 21, No. 13, pp. 901-924, 1970.

Williamson, J.R., et al., "Inhibition of fatty acid stimulation of gluconeogenesis by (+)-decanoylcarnitine in perfused rat liver". Diabetes, 1968. 17(4): p. 194-208.

* cited by examiner

Figure
Fatty acid metabolism pathway
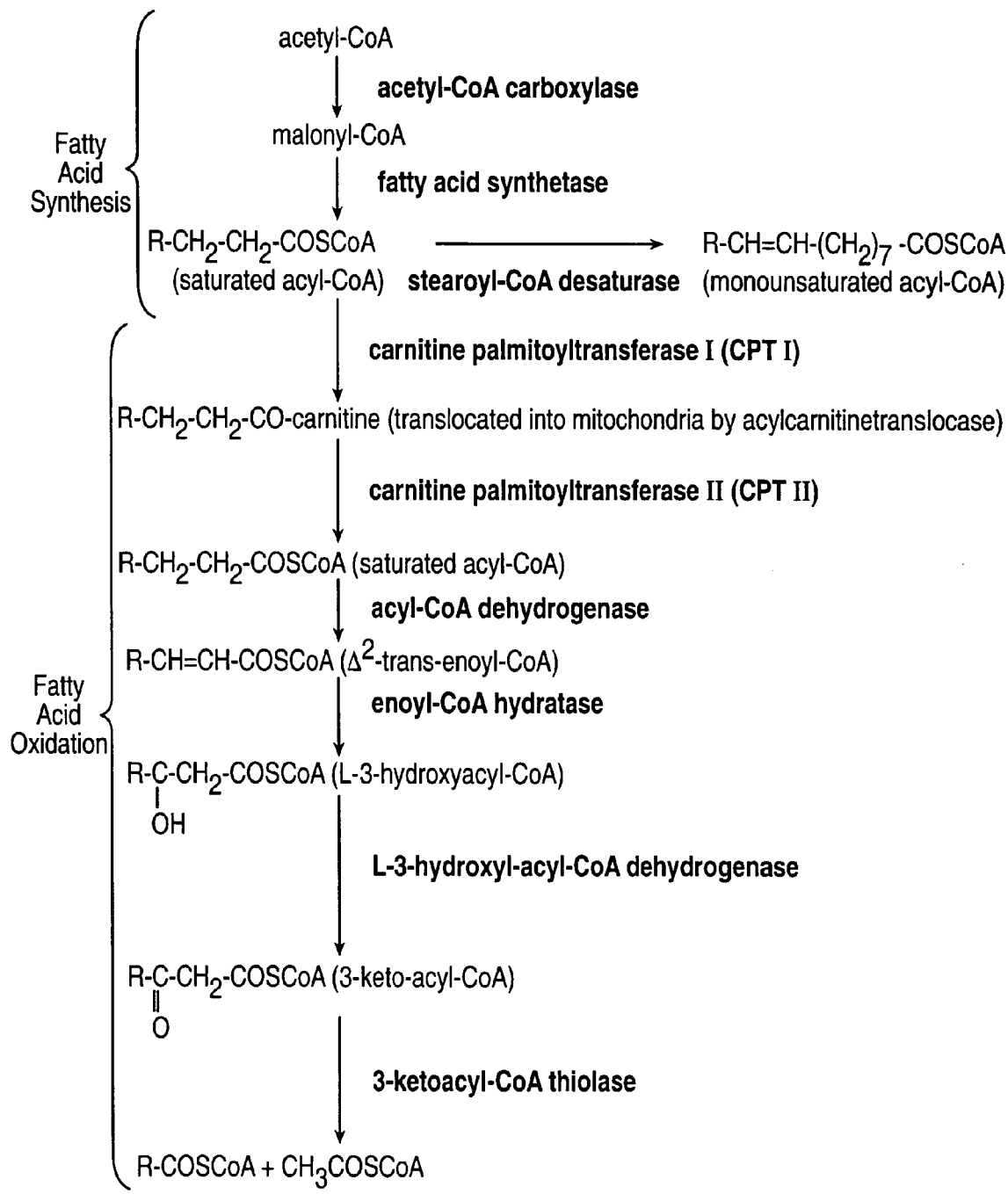

REDUCTION OF HAIR GROWTH

CROSS-REFERENCE TO RELATED APPLICATION

This application is a continuation-in-part of U.S. Ser. No. 10/430,988, filed May 6, 2003 now abandoned, and entitled "Reduction of Hair Growth", which is a continuation-in-part of U.S. Ser. No. 10/059,466, filed Jan. 29, 2002 now abandoned, and entitled "Reduction of Hair Growth"

BACKGROUND

The invention relates to reducing hair growth in mammals, particularly for cosmetic purposes.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; and Shander et al., U.S. Pat. No. 5,132,293.

Fatty acids can regulate biological functions by providing metabolic fuel and/or being a part of the structural components of cellular membranes. The extent of this regulation depends on the tissue. In mammalian cells fatty acid metabolism generally includes fatty acid synthesis and fatty acid oxidation. The fatty acid synthesis occurs in cell cytosol and produces long-chain fatty acids for various cellular functions. The oxidation pathway occurs in the cellular compartment mitochondria and generates energy to support various cellular processes.

The fatty acid oxidation is a metabolic process under which ATP is formed by oxidative phosphorylation. In heart and skeletal muscle, fatty acid oxidation provides the major source of energy under a variety of conditions. For example, during prolonged fasting and starvation, fatty acid oxidation provides acetyl-CoA for the synthesis of "ketone bodies" that are used as an alternate fuel in some tissues, such as brain, when the supply of glucose is low.

Long-chain fatty acids such as palmitic acid and stearic acid are major substrates for fatty acid oxidation. The pathway for the fatty acid oxidation is summarized in the FIGURE. In mammalian cells, free fatty acids are converted to CoA thioesters catalyzed by acyl-CoA synthetase. Because the inner mitochondrial membrane is a barrier to acyl-CoA, fatty acyl residues are carried across this membrane as carnitine esters. Carnitine palmitoyltransferase I (CPT I), which is located at the outer mitochondrial membrane, transfers fatty acid acyl residues from CoA to L-carnitine. The resultant fatty acyl carnitines pass through the inner mitochondrial membrane via carnitine:acylcarnitine translocase. Once in the matrix, carnitine palmitoyltransferase II (CPT II) catalyzes the transfer of fatty acyl residues back from carnitine to CoA-SH. Acyl-CoA, formed in the matrix, is the substrate for fatty acid oxidation cycle that yields acetyl-CoA, NADH and $FADH_2$. The latter two compounds are oxidized by the mitochondrial electron transport chain and acetyl-CoA is oxidized to $CO_2$ by tricarboxylic acid cycle. Hence, the complete oxidation of a long-chain fatty acid can produce several ATP molecules, which are utilized for energy-requiring cellular processes. The enzymes catalyzing the repetitive reactions of the fatty acid oxidation cycle include acyl-CoA dehydrogenase, enoyl-CoA hydratase, L-3-hydroxyacyl-CoA dehydrogenase and 3-ketoacyl-CoA thiolase. Long-chain fatty acids are not only metabolic fuel for certain tissues but are also structural components of cellular membranes. Most long-chain fatty acids are derived from either diet or de novo synthesis. Fatty acid synthesis, which produces long-chain fatty acids from acetyl-CoA, is mainly carried out in liver and adipose tissue. The synthesized fatty acids are converted to triacylglycerols, phospholipids and sphingolipids. Most triacylglycerols are stored in adipose tissues as energy source for other tissues such as skeletal muscle. Phospholipids and sphingolipids end up as constituents of cellular membrane.

The majority of long-chain fatty acids synthesized in mammalian cell are saturated fatty acids (e.g. palmitic acid) and monounsaturated fatty acids (e.g., oleic acid). Two major steps carry out the biosynthesis of saturated fatty acids from acetyl-CoA. The first step is the conversion of acetyl-CoA to malonyl-CoA, a reaction catalyzed by acetyl-CoA carboxylase. It is a rate-limiting step in the biosynthesis of fatty acids. The second step is the conversion of acetyl-CoA and malonyl-CoA to long-chain fatty acids, catalyzed by fatty acid synthetase in the presence of NADPH. Mammalian fatty acid synthetase are multifunctional proteins typically consisting of two identical subunits. The reaction starts from acetyl-CoA and malonyl-CoA and involves sequential reactions and acyl intermediates. Six more malonyl groups react successively at the carboxyl end of the growing fatty acid chain to form the end product palmitic acid.

Several inhibitors of acetyl-CoA carboxylase and fatty acid synthetase have been developed and used to inhibit fatty acid synthesis in various tissues. Among these, 5-(tetradecyloxy)-2-furoic acid (TOFA) and cerulenin have been commonly used to inhibit fatty acid synthesis both in vivo and in vitro. It has been shown that TOFA is converted to its CoA ester by isolated hepatocytes and the resulting compound 5-(tetradecyloxy)-2-furoyl-CoA is an effective inhibitor of acetyl-CoA carboxylase. Cerulenin can bind one of the functional domains of fatty acid synthetase and inhibit its activity.

Palmitoleic and oleic acids are major monounsaturated fatty acids in animal tissues. Palmitic and stearic acid serve as precursors to their synthesis. A cis double bond is introduced in the $\Delta^9$ position (between carbons 9 and 10) of these molecules by the stearoyl-CoA desaturase complex to form the respective monounsaturated fatty acid. The desaturase complex is located in the endoplasmic reticulum and consists of three proteins (i) cytochrome $b_5$ reductase, (ii) cytochrome $b_5$ and (iii) the desaturase. During desaturation, the electrons flow sequentially from NAD(P)H, through cytochrome b5 reductase, to cytochrome b5, to the stearoyl-CoA desaturase, and finally to active oxygen which is reduced to $H_2O$.

There are two kinds of fatty acids—essential and non-essential. Non-essential fatty acids are synthesized as described above. Essential fatty acids are not synthesized by cells but instead are derived from dietary sources. Essential fatty acids include, for example, linoleic acid and linolenic acid.

Both essential and non-essential fatty acids are transported into cells across the cellular membranes (the outer membrane of the cells). The transport may be by passive diffusion or by involvement of fatty acid transport proteins (FATP) on the cellular membranes. The transport of fatty acids across cellular membranes also includes the uptake of fatty acids by tissues.

BRIEF DESCRIPTION OF THE DRAWINGS

The FIGURE is a general summary of fatty acid metabolism.

SUMMARY

In one aspect, the invention provides a method (typically a cosmetic method) of reducing unwanted mammalian (preferably human) hair growth by applying to the skin a compound that inhibits fatty acid metabolism in an amount effective to reduce hair growth. The unwanted hair growth may be undesirable from a cosmetic standpoint or may result, for example, from a disease or an abnormal condition (e.g., hirsutism). The compound may be, for example, an inhibitor of an enzyme involved in fatty acid oxidation or fatty acid synthesis.

In another aspect, the invention provides a method (typically a cosmetic method) of reducing unwanted mammalian (preferably human) hair growth by applying to the skin a compound that inhibits transport of a fatty acid across a cellular membrane in an amount effective to reduce hair growth. The unwanted hair growth may be undesirable from a cosmetic standpoint or may result, for example, from a disease or an abnormal condition (e.g., hirsutism). The compound may be, for example, a compound that inhibits activity of a fatty acid transport protein on the cellular membrane.

Typically, in practicing the aforementioned methods, the compound will be included in a topical composition along with a dermatologically or cosmetically acceptable vehicle. Accordingly, the present invention also relates to topical compositions comprising a dermatologically or cosmetically acceptable vehicle and the compound in an amount effective to reduce hair growth.

In addition, the present invention relates to the use of a compound that inhibits fatty acid metabolism and/or a compound that inhibits transport of a fatty acid across a cellular membrane for the manufacture of a therapeutic topical composition for reducing hair growth.

In another aspect, the invention provides a method (typically a cosmetic method) of reducing unwanted mammalian (preferably human) hair growth by reducing the activity of a fatty acid transport protein on a cellular membrane in an amount effective to reduce hair growth. The unwanted hair growth may be undesirable from a cosmetic standpoint or may result, for example, from a disease or an abnormal condition (e.g., hirsutism).

Other features and advantages of the invention may be apparent from the description of the preferred embodiments thereof, and from the claims.

DETAILED DESCRIPTION

An example of a preferred composition includes at least one inhibitor of an enzyme involved in fatty acid oxidation or fatty acid synthesis in a cosmetically and/or dermatologically acceptable vehicle. The composition may be a solid, semi-solid, or liquid. The composition may be, for example, a cosmetic and dermatologic product in the form of an, for example, ointment, lotion, foam, cream, gel, or solution. The composition may also be in the form of a shaving preparation or an aftershave.

Examples of inhibitors of carnitine palmitoyltransferase I (CPT I) include adriamycin; D,L-aminocarnitine; acylamino carnitines; decanoylcarnitine; amiodarone; 2-bromopalmitic acid; 2-bromopalmitoylcarnitine; 2-bromopalmitoyl-CoA; 2-bromomyristoylthiocarnitine; emeriamine; erucic acid; erucylcarnitine; etomoxir; etomoxiryl-CoA; glyburide; hemiacetylcarnitinium chloride; hemipalmitoylcanitinium chloride; 3-hydroxy-5-5-dimethylhexanoic acid (HDH); methyl palmoxirate (methyl-2-tetradecylglycidate); 2-tetradecylglycidic acid; oxfenicine; perhexiline; 2[5(4-chlorophenyl)pentyl]-oxirane-2-carboxylic acid (POCA); 2-[3-(3-trifluoromethylphenyl)-propyl]oxiran-2-carbonyl-CoA; 2-[5-(4-chlorophenyl)pentyl]-oxiran-2-carbonyl-CoA; 2-(5-phenylpentyl)oxiran-2-carbonyl-CoA; 2-tetradecyloxiran-2-carbonyl-CoA; 8,N,N-diethylamino-octyl-3,4,5-trimethoxybenzoate (TMB-8); tolbutamide; and trimetazidine.

Examples of inhibitors of acyl-CoA dehydrogenase include hypoglycin; 2-mercaptoacetic acid; 3-mercaptopropionic acid; methylenecyclopropylacetic acid (MCPA); methylenecyclopropylformic acid ($C_6MCPA$); spiropentaneacetic acid; 3-methyleneoctanoyl-CoA; and 3-methyl-trans-2-octenoyl-CoA.

Examples of inhibitors of 3-ketoacyl-CoA thiolase include 4-bromocrotonic acid; 2-bromooctanoic acid; 2-bromo-3-ketooctanoyl-CoA; 4-bromo-2-octenoic acid and 4-pentenoic acid.

Examples of inhibitors of acetyl-CoA carboxylase include 5-(tetradecyloxy)-2-furoic acid (TOFA); sethoxydim (cyclohexanedione); medica 16 (β,β'-methyl-substituted hexadecanedioic acid); 2-n-pentadecyl-benzimidazole-5-carboxylate; and 2-methyl-2-(p-(1,2,3,4-tetrahydro-naphthyl)phenoxy)propionic acid (TPIA).

Examples of inhibitors of fatty acid synthethase include cerulenin; carbacerulenin; and 3-carboxy-4-alkyl-2-methylenebutyrolactone (C75).

An example of an inhibitor of stearoyl-CoA desaturase is sterculic acid.

The inhibitors just mentioned are known.

A chemical name for an inhibitor also includes pharmaceutically acceptable salts of the inhibitor.

An inhibitor of an enzyme inhibits the catalytic activity of the enzyme, for example, by acting on the enzyme itself (direct inhibition) or by acting on the substrate targeted by the enzyme (a form of direct inhibition).

The composition may include more than one inhibitor of an enzyme involved in fatty acid oxidation or fatty acid synthesis. In addition, the composition may include one or more other types of hair growth reducing agents, such as those described in U.S. Pat. No. 4,885,289; U.S. Pat. No.

4,720,489; U.S. Pat. No. 5,132,293; U.S. Pat. No. 5,096,911; U.S. Pat. No. 5,095,007; U.S. Pat. No. 5,143,925; U.S. Pat. No. 5,328,686; U.S. Pat. No. 5,440,090; U.S. Pat. No. 5,364,885; U.S. Pat. No. 5,411,991; U.S. Pat. No. 5,648,394; U.S. Pat. No. 5,468,476; U.S. Pat. No. 5,475,763; U.S. Pat. No. 5,554,608; U.S. Pat. No. 5,674,477; U.S. Pat. No. 5,728,736; U.S. Pat. No. 5,652,273; WO 94/27586; WO 94/27563; and WO 98/03149, all of which are incorporated herein by reference.

The concentration of the inhibitor in the composition may be varied over a wide range up to a saturated solution, preferably from 0.1% to 30% by weight or even more; the reduction of hair growth increases as the amount of inhibitor applied increases per unit area of skin. The maximum amount effectively applied is limited only by the rate at which the inhibitor penetrates the skin. The effective amounts may range, for example, from 10 to 3000 micrograms or more per square centimeter of skin.

The vehicle can be inert or can possess cosmetic, physiological and/or pharmaceutical benefits of its own. Vehicles can be formulated with liquid or solid emollients, solvents, thickeners, humectants and/or powders. Emollients include stearyl alcohol, mink oil, cetyl alcohol, oleyl alcohol, isopropyl laurate, polyethylene glycol, petroleum jelly, and myristyl myristate. Solvents include ethyl alcohol, isopropanol, acetone, diethylene glycol, ethylene glycol, dimethyl sulfoxide, and dimethyl formamide.

The composition also can include components that enhance the penetration of the inhibitor into the skin and/or to the site of action. Examples of penetration enhancers include urea, polyoxyethylene ethers (e.g., Brij-30 and Laureth-4), 3-hydroxy-3,7,11-trimethyl-1,6,10-dodecatriene, terpenes, cis-fatty acids (e.g., oleic acid, palmitoleic acid), acetone, laurocapram, dimethylsulfoxide, 2-pyrrolidone, oleyl alcohol, glyceryl-3-stearate, propan-2-ol, myristic acid isopropyl ester, cholesterol, and propylene glycol. A penetration enhancer can be added, for example, at concentrations of 0.1% to 20% or 0.5% to 5% by weight.

The composition also can be formulated to provide a reservoir within or on the surface of the skin to provide for a continual slow release of the inhibitor. The composition also may be formulated to evaporate slowly from the skin, allowing the inhibitor extra time to penetrate the skin.

EXAMPLE 1

A composition prepared containing 10% by weight of palmitoyl DL carnitine in a vehicle containing 68% water, 16% ethanol, 5% propylene glycol, 5% dipropylene glycol, 4% benzyl alcohol and 2% propylene carbonate.

EXAMPLE 2

A composition prepared containing 10% by weight of amiodarone in a vehicle containing 68% water, 16% ethanol, 5% propylene glycol, 5% dipropylene glycol, 4% benzyl alcohol and 2% propylene carbonate.

EXAMPLE 3

A composition prepared containing 10% by weight of DL-decanoylcarnitine chloride in a vehicle containing 80% ethanol, 17.5% water, 2% propylene glycol dipelargonate (Emerest 2388), and 0.5% propylene glycol.

EXAMPLE 4

A composition prepared containing 2.5% by weight of perhexiline in a vehicle containing 80% ethanol, 17.5% water, 2% propylene glycol dipelargonate (Emerest 2388), and 0.5% propylene glycol.

EXAMPLE 5

A composition prepared containing 10% by weight of glynbenclamide in a vehicle containing 70% ethanol, 30% propylene glycol.

EXAMPLE 6

A composition prepared containing 10% by weight of 4-tert-butylbenzoic acid in a vehicle containing 64% ethanol, 20% dimethyl sulfoxide 14% water, 1.6% propylene glycol dipelargonate (Emerest 2388), and 0.4% propylene glycol.

EXAMPLE 7

A composition prepared containing 10% by weight of 4-pentenoic acid in a vehicle containing 68% water, 16% ethanol, 5% propylene glycol, 5% dipropylene glycol, 4% benzyl alcohol and 2% propylene carbonate.

EXAMPLE 8

A composition prepared containing 2% by weight of methyl palmoxirate in a vehicle containing 80% ethanol, 17.5% water, 2% propylene glycol dipelargonate (Emerest 2388), and 0.5% propylene glycol.

EXAMPLE 9

A composition prepared containing 3% by weight of 4-bromocrotonic acid in a vehicle containing 80% ethanol, 17.5% water, 2% propylene glycol dipelargonate (Emerest 2388), and 0.5% propylene glycol.

EXAMPLE 10

A composition containing an inhibitor of carnitine palmitoyl transferase-I at a dose of 1–10% by weight in a cream based vehicle containing water 80.84%, glyceryl stearate 4.24%, polyethylene glycol 100-stearate 4.09%, cetearyl alcohol 3.05%, ceteareth-20 2.5%, mineral oil 2.22%, stearyl alcohol 1.67%, dimethicone 0.56%.

EXAMPLE 11

Any one or more of the previous examples in combination with one or more of the penetration enhancers selected from urea, propan-2-ol, polyoxyethylene ethers, terpenes, cis-fatty acids (oleic acid, palmitoleic acid), acetone, laurocapram, dimethylsulfoxide, 2-pyrrolidone, oleyl alcohol, glyceryl-3-stearate, cholesterol, myristic acid isopropyl ester, propylene glycol.

The composition should be topically applied to a selected area of the body from which it is described to reduce hair growth. For example, the composition can be applied to the face, particularly to the beard area of the face, i.e., the cheek, neck, upper lip, and chin. The composition also may be used as an adjunct to other methods of hair removal including shaving, waxing, mechanical epilation, chemical depilation, electrolysis and laser-assisted hair removal.

The composition can also be applied to the legs, arms, torso or armpits. The composition is particularly suitable for reducing the growth of unwanted hair in women having hirsutism or other conditions. In humans, the composition should be applied once or twice a day, or even more frequently, to achieve a perceived reduction in hair growth. Perception of reduced hair growth could occur as early as 24 hours or 48 hours (for instance, between normal shaving intervals) following use or could take up to, for example, three months. Reduction in hair growth is demonstrated when, for example, the rate of hair growth is slowed, the need for removal is reduced, the subject perceives less hair on the treated site, or quantitatively, when the weight of hair removed (i.e., hair mass) is reduced.

Golden Syrian Hamster Assay

Male intact Golden Syrian hamsters are considered acceptable models for human beard hair growth in that they display oval shaped flank organs, one on each side, each about 8 mm. in major diameter. These organs produce fine light colored hair typical of the animal pelage found on the body. In response to androgens the flank organs produce dark coarse hair similar to male human beard hair. To evaluate the effectiveness of a composition in reducing hair growth, the flank organs of each of a group of hamsters are depilated by applying a thioglycolate based chemical depilatory (Surgex) and/or shaved. To one organ of each animal 10 μl. of vehicle alone once a day is applied, while to the other organ of each animal an equal amount of vehicle containing the compound under evaluation is applied. After three weeks of topical applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay or "hair mass" assay. Preferred compositions provide a reduction in hair growth of at least about 15% and more preferably at least about 35%, when tested in the Golden Syrian hamster assay.

Human Hair Follicle Growth Assay

Tissue source—Human skin was obtained from a plastic surgeon as a by-product of face-lift procedures. Immediately after removal, the skin was placed in Williams E medium containing antibiotics and refrigerated. The Williams E medium is a commercially obtained medium which has been formulated with essential nutrients for maintaining viability of tissues or cells such as of hair follicle in an in-vitro environment.

Hair Follicle Isolation and Culture—Human hair follicles in growth phase (anagen) were isolated from face-lift tissue under a dissecting scope using a scalpel and watchmakers forceps. The skin was sliced into thin strips exposing 2–3 rows of follicles that could readily be dissected. Follicles were placed into 0.5 ml Williams E medium supplemented with 2 mM L-glutamine, 10 μg/ml insulin, 100 ng/ml hydrocortisone, 100 units penicillin, 0.1 mg/ml streptomycin and 0.25 μg/ml amphotericin B. The follicles were incubated in 24 well plates (1 follicle/well) at 37° C. in an atmosphere of 5% $CO_2$ and 95% air. Hair follicles were video recorded in the 24-well plates under the dissecting scope under a power of 10×. Typically, hair follicle lengths were measured on day 0 (day follicles were placed in culture) and again on day 7. When testing compounds, the compound was included in the culture medium from time 0 and remained in the medium throughout the course of the experiment. The length of hair follicles was assessed using an image analysis software system (Jasc Image Robot).

Assay of Carnitine Palmitoyl Transferase-I (CPT-I)

Two different enzyme assays were used to quantify the activity of CPT-I in hair follicles:

Method-I

Hair follicle rich fraction from hamster flank organs are homogenized in Buffer A (200 mM mannitol, 10 mM sucrose, 5 mM MOPS pH 7.4). The homogenate is centrifuged at 2000 rpm for 10 minutes. The supernatant is removed and centrifuged at 7000 rpm for 30 minutes. The pellet is resuspended in Buffer B (20 mM Tris-HCl, pH 7.4), 400 mM sucrose, 80 mM KCl, 2 mM EDTA, 2.6 mg/ml fatty acid free BSA). 30 μl of the resuspended pellet is added to 35 μl of DMSO or one of the inhibitors diluted in DMSO so that the final concentration is 5 mM. After a 15 min preincubation, the following are added; 35 μl of 1.7 mM palmitoyl Co-A (34% water and 66% Buffer B), 10 μl of 5 mM L-carnitine (in buffer B with 0.5 μCi $^3$H-carnitine). The reaction is then placed in a 37° C. water bath for 30 minutes. At the end of 30 minutes the reaction is stopped by the addition of 150 μl cold 1N HCl. This is followed by the addition of 250 μl water to each sample. Butanol (500 μl) is then added to each sample and the samples are centrifuged for 2 minutes at 10,000×g. 300 μl of the butanol layer is transferred to a new centrifuge tube and 250 μl of water is added. 200 μl of the organic phase is added to a scintillation vial containing 12 ml of scintillation cocktail. The radioactivity is determined using a scintillation counter.

Method II

The enzyme activity of carnitine palmitoyl transferase-I (CPT-I) was also determined in the isolated mitochondrial fraction. Isolation of mitochondria from the hair follicle rich fraction of flank organs was accomplished by conventional differential centrifugation in 0.25 M sucrose, 10 mM Tris-HCl, pH 7.4 and 1 mM EDTA after tissues were homogenized by polytron homogenizer and Dounce tissue grinder. The pellet obtained at 7000 g was washed two times and finally suspended at 40–80 mg/ml. Carnitine palmitoyltransferase was measured as the rate of conversion of palmitoyl-CoA and [$^3$H]$CH_3$-L-carnitine into palmitoyl-[$^3$H]$CH_3$-1-carnitine. The incubation mixture initially contained 12.5 μmol of Tris-HCl (pH 7.2), 15 μmol of KCl, 3.1 μmol of KCN, 6.2 μmol of glutathione, 15 nmol of CoA, 2 mmol of $MgSO_4$, 2 μmol of ATP (pH 6.8) in volume of 0.425 ml. To this mixture 50 μl of mitochondria were added, followed by preincubation at 37° C. for 10 minutes in the presence or absence of the enzyme inhibitor methyl palmoxirate (dissolved in DMSO). After preincubation, the enzyme reaction was initiated by the addition of 25 μl of 2 mM palmitoyl-CoA and 25 μl of 4 mM [$^3$H]$CH_3$-L-carnitine. The reaction was stopped after 30 minutes with 1 ml 1N HCl and palmitoyl-[$^3$H]$CH_3$-L-carnitine was extracted into n-butanol. The radioactivity was determined using scintillation spectrometry.

Assay of 3-ketoacyl-CoA Thiolase:

Mitochondria were isolated as described in previous section (D) and preincubated with 100 μM 4-bromocrotonic acid for 5 min. Aliquots of the mitochondrial suspension (50 µl) were rapidly frozen in dry ice and stored at −80° C. until enzyme activities were assayed as described below. To insure the complete disruption of mitochondria, Triton X-100 (0.06%) was added to all assay mixtures. The activity of thiolase was determined by spectrophotometrically following the disappearance of the $Mg^{2+}$-enolate complex at 303 nm. The enzyme assay was performed at 25° C. The reaction mixture contained 0.1 M Tris-HCl (pH 8.2), 25 mM $MgCl_2$, 30 mM KCl, 0.06% Triton X-100, bovine serum albumin (0.13 mg/ml), 70 µM CoA and 33 µM acetoacetyl-CoA. Molar extinction coefficient of 21,400 $cm^{-1}M^{-1}$ was used to calculate the rates determined with acetoacetyl-CoA.

Assay of Acyl-CoA Dehydrogenase

Mitochondria were isolated as described previously and preincubated with 1 mM methylenecyclopropylacetic acid (MCPA) for 5 min. Mitochondria were diluted to 1 mg/ml in 0.1% cholic acid and 50 mM phosphate buffer, pH 7.4. Acyl-CoA dehydrogenase activity was determined in a reaction medium containing 34 mM potassium phosphate (pH 7.2), 0.15 mM cytochrome c, 3.75 µM rotenone, 200 µM octanoyl-CoA and 3 mM phenazine ethosulfate. The assay was carried out at 37° C. in a final volume of 0.5 ml. Octanoyl-CoA was used as a substrate and converted to 2-enol-CoA by acyl-CoA dehydrogenase. The electron generated from the reaction was transferred to cytochrome c. The absorbance of reduced cytochrome c was monitored at 550 nm. Molar extinction coefficient of 19 $cm^{-1}mM^{-1}$ was used to calculate the rate of reduced cytochrome c formation.

Results:

The hair growth inhibitory efficacy of inhibitors of enzymes involved in fatty acid oxidation was evaluated in the Golden Syrian Hamster assay. Inhibitors of carnitine palmitoyltransferase I (CPT I), acyl-CoA dehydrogenase, and 3-ketoacyl-CoA thiolase were evaluated in this assay. The data indicate that inhibition of fatty acid oxidation causes reduction of hair growth (Table I). A representative inhibitor for each enzyme also was evaluated in human hair follicle growth assay. The data show human hair growth inhibition by these compounds in this in-vitro model (Table II). In addition, cellular mitochondrial fraction of hamster flank organs hair follicles was isolated, and the enzyme activities of CPT I, acyl-CoA dehydrogenase and 3-ketoacyl-thiolase were measured in the presence and absence of select inhibitors. The results (Tables III, IV, V and VI) indicate that the activity of each enzyme can be detected in the mitochodrial fraction of hamster flank organ, and that the inhibitors reduce the activity of each enzyme. Taken together, the data indicate that the inhibition of enzymes involved in fatty acid oxidation results in a reduction of hair growth.

Inhibitors of two major fatty acid synthesis pathways, saturated fatty acid synthesis and monounsaturated fatty acid synthesis, also were tested in human hair follicle growth assay and/or the hamster hair mass assay. The data from these studies indicate that cerulenin, an inhibitor of fatty acid synthetase, can inhibit human hair follicle growth in vitro with marked efficacy (Table VII). The data also indicate that methyl sterculate, an inhibitor of stearoyl-CoA desaturase, can reduce hair growth both in vivo and in vitro as shown (Table VIII and IX).

TABLE I

Inhibition of hamster hair mass by inhibitors of fatty acid oxidation

| Compound | Dose (%) | Vehicle | Treated (mg) | Control (mg) | % Inhibition |
| --- | --- | --- | --- | --- | --- |
| palmitoyl DL carnitine | 10.0 | A* | 0.29 ± 0.1 | 1.29 ± 0.17 | 73 ± 15 |
| DL-decanoylcarnitine chloride | 10.0 | B* | 0.94 ± 0.12 | 2.27 ± 0.21 | 58 ± 5 |
| amiodarone | 7.5 | A* | 1.62 ± 0.9 | 2.98 ± 0.62 | 44 ± 28 |
| 4-tert-butylbenzoic acid | 10.0 | C* | 1.10 ± 0.12 | 2.14 ± 0.14 | 46 ± 8 |
| glynbenclamide | 10.0 | D* | 1.40 ± 0.32 | 1.96 ± 0.31 | 32 ± 8 |
| perhexiline | 2.5 | B* | 2.28 ± 0.77 | 3.06 ± 0.87 | 23 ± 25 |
| 4-pentenoic acid | 10.0 | A* | 1.10 ± 0.12 | 2.14 ± 0.14 | 46 ± 8 |
| methyl palmoxirate | 2.0 | B* | 0.56 ± 0.12 | 1.70 ± 0.32 | 66 ± 4 |
| 4-bromocrotonic acid | 3.0 | B* | 1.25 ± 0.37 | 1.86 ± 0.31 | 37 ± 14 |
| 2-propylpentanoic acid | 20.0 | A* | 2.68 ± 0.20 | 0.87 ± 0.08 | 67 ± 3 |
| methylenecyclopropyl-acetic acid (MCPA) | 5.0 | B* | 2.3 ± 0.26 | 2.76 ± 0.2 | 16 ± 7 |

*Vehicles:
A - 68% water, 16% ethanol, 5% propylene glycol, 5% dipropylene glycol, 4% benzyl alcohol and 2% propylene carbonate.
B - 80% ethanol, 17.5% water, 2% propylene glycol dipelargonate (Emerest 2388), and 0.5% propylene glycol.
C - 64% ethanol, 20% dimethyl sulfoxide 14% water, 1.6% propylene glycol dipelargonate (Emerest 2388), and 0.4% propylene glycol.
D - 70% ethanol, 30% propylene glycol.

TABLE II

Inhibition on human hair follicle growth by inhibitors of fatty acid oxidation

| Inhibitor | Dose (mM) | Hair follicle length increase (mm) | % nhibition |
| --- | --- | --- | --- |
| control (for methyl palmoxirate) | — | 1.26 ± 0.65 | 0.00 |
| methyl palmoxirate | 0.1 | 0.54 ± 0.3 | 57 ± 24 |
| control (for MCPA) | — | 1.80 ± 0.50 | 0.00 |
| methylenecyclopropyl-acetic acid (MCPA) | 0.5 | 1.21 ± 0.26 | 33 ± 14 |
| control (for 4-bromocrotonic acid) | — | 1.13 ± 0.15 | 0.00 |
| 4-bromocrotonic acid | 0.03 | 0.06 ± 0.06 | 95 ± 5 |

TABLE III

Inhibition of Carnitine palmitoyltransferase I (CPT I)*

| Inhibitor | pmol product/mg protein | % inhibition |
|---|---|---|
| control | 0.75 | 0 |
| glybenclamide (5 mM) | 0.00 | 100 |
| malonyl CoA (5 mM) | 0.59 | 22 |
| tolbutamide (5 mM) | 0.07 | 90 |
| 2-bromopalmitic acid (5 mM) | 0.07 | 91 |
| perhexiline (5 mM) | 0.10 | 86 |

*The CPT-I assay method-I was used for these analyses.

TABLE IV

Inhibition of Carnitine palmitoyltransferase I (CPT I)

| Inhibitor | pmol product/mg protein | % inhibition |
|---|---|---|
| control (oxfenicine) | 1.15 | 0 |
| oxfenicine (1 mM) | 0.64 | 44 |
| control (for methyl palmoxirate) | 0.6 | 0 |
| methyl palmoxirate (50 mM) | 0.146 | 92.3 |

The CPT-I assay method-II was used for these analyses.

TABLE V

Inhibition of acyl-CoA dehydrogenase by methylenecyclopropylacetic acid

| Inhibitor | nmol product/mg protein | % inhibition |
|---|---|---|
| control | 1.62 | 0 |
| methylenecyclopropyl-acetic acid (MCPA) (1 mM) | 0.497 | 69.3 |

TABLE VI

Inhibition of 3-ketoacyl-CoA thiolase by 4-bromocrotonic acid

| Inhibitor | nmol product/mg protein | % inhibition |
|---|---|---|
| control | 0.87 | 0 |
| 4-bromocrotonic acid (0.5 mM) | 0.128 | 85.2 |

TABLE VII

Inhibition of human hair follicle growth by an inhibitor of fatty acid synthetase

| Inhibitor | Dose (µM) | Hair follicle length increase (mm) | % Inhibition |
|---|---|---|---|
| control | — | 1.04 ± 0.22 | 0 |
| cerulenin | 10 | 0.06 ± 0.05 | 93.7 ± 5.6 |

TABLE VIII

Inhibition of hamster hair mass by an inhibitor of stearoyl-CoA desaturase

| Compound | Dose (%) | Vehicle | Treated (mg) | Control (mg) | % Inhibition |
|---|---|---|---|---|---|
| methyl sterculate | 2.5 | E* | 1.4 ± 0.2 | 2.65 ± 0.3 | 45.1 ± 6.8 |

*Vehicles: E - 90% ethanol, 10% polyethylene glycol.

TABLE IX

Inhibition of human hair follicle growth by an inhibitor of stearoyl-CoA desaturase

| Inhibitor | Dose | Hair follicle length (increase mm) | % Inhibition |
|---|---|---|---|
| control | — | 1.45 ± 0.52 | 0 |
| methyl sterculate | 1 mM | 0.59 ± 0.29 | 59.3 ± 0.2 |

Other embodiments are within the claims.

What is claimed is:

1. A method of reducing mammalian hair growth which comprises selecting an area of skin from which reduced hair growth is desired; and applying to said area of skin a dermatologically acceptable composition comprising methyl palmoxirate.

2. The method of claim 1, wherein the concentration of methyl palmoxirate in said composition is between 0.1% and 30%.

3. The method of claim 1, wherein methyl palmoxirate is applied to the skin in an amount of from 10 to 3000 micrograms per square centimeter of skin.

4. The method of claim 1, wherein said mammal is a human.

5. The method of claim 4, wherein said area of skin is on the face of a human.

6. The method of claim 5, wherein the composition is applied to the area of skin in conjunction with shaving.

7. The method of claim 4, wherein said area of skin is on a leg of the human.

8. The method of claim 4, wherein said area of skin is on an arm of the human.

9. The method of claim 4, wherein said area of skin is in an armpit of the human.

10. The method of claim 4, wherein said area of skin is on the torso of the human.

11. The method of claim 1, wherein the composition is applied to an area of skin of a woman with hirsutism.

12. The method of claim 1, wherein said hair growth comprises androgen stimulated hair growth.

13. The method of claim 1, wherein the composition further includes a second compound that also causes a reduction in hair growth.

* * * * *